(12) United States Patent
Tonomura et al.

(10) Patent No.: US 8,178,710 B2
(45) Date of Patent: May 15, 2012

(54) SILYL (METH)ACRYLATE COMPOUND CONTAINING A SILOXY GROUP HAVING A BULKY SUBSTITUENT AND ITS PRODUCTION METHOD

(75) Inventors: Yoichi Tonomura, Joetsu (JP); Tohru Kubota, Joetsu (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 371 days.

(21) Appl. No.: 12/606,520

(22) Filed: Oct. 27, 2009

(65) Prior Publication Data

US 2010/0105938 A1   Apr. 29, 2010

(30) Foreign Application Priority Data

Oct. 29, 2008   (JP) ................................ 2008-278151

(51) Int. Cl.
*C07F 7/18* (2006.01)
(52) U.S. Cl. ......... 556/442; 556/406; 556/437; 556/441
(58) Field of Classification Search .................. 556/406, 556/437, 441, 442
See application file for complete search history.

(56) References Cited

U.S. PATENT DOCUMENTS 4,593,055 A    6/1986   Gitlitz et al.

FOREIGN PATENT DOCUMENTS

| | | |
|---|---|---|
| EP | 1016681 A2 | 7/2000 |
| EP | 1380611 A1 | 1/2004 |
| EP | 1431301 A1 | 6/2004 |
| EP | 1614722 A1 | 1/2006 |
| JP | 63-253090 A | 10/1988 |
| JP | 3053081 B2 | 6/2000 |
| WO | 03/027124 A1 | 4/2003 |
| WO | 2004/007591 A1 | 1/2004 |

OTHER PUBLICATIONS

European Search Report dated Feb. 18, 2010, issued in corresponding European Patent Application No. 09013586.4.

*Primary Examiner* — Elvis O Price
(74) *Attorney, Agent, or Firm* — Westerman, Hattori, Daniels & Adrian LLP

(57) ABSTRACT

A silyl (meth)acrylate compound containing a siloxy group having a bulky substituent is provided. The compound is represented by the following general formula (1):

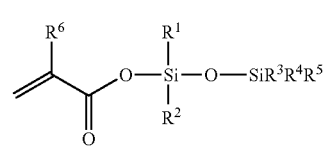

wherein $R^1$ and $R^2$ are independently a $C_{3-10}$ monovalent branched hydrocarbon group having a hydrocarbon group at α or β position or a monovalent $C_{3-10}$ cyclic hydrocarbon group; $R^3$, $R^4$, and $R^5$ are independently an unsubstituted or substituted $C_{1-20}$ hydrocarbon group or a siloxy group represented by the following general formula (2):

$$-OSiR^7R^8R^9 \qquad (2)$$

wherein $R^7$, $R^8$, and $R^9$ are independently an unsubstituted or substituted $C_{1-20}$ hydrocarbon group; and $R^6$ is hydrogen atom or methyl group. This compound is hydrolyzed at a reduced speed, and use of a polymer obtained by copolymerization with an alkyl methacrylate is capable of suppressing attachment of marine organisms to the ship with no or reduced biocide, and this polymer is useful for a hydrolytic self-polishing paint.

6 Claims, 14 Drawing Sheets

SILYL (METH)ACRYLATE COMPOUND CONTAINING A SILOXY GROUP HAVING A BULKY SUBSTITUENT AND ITS PRODUCTION METHOD

CROSS-REFERENCE TO RELATED APPLICATION

This non-provisional application claims priority under 35 U.S.C. §119(a) on Patent Application No. 2008-278151 filed in Japan on Oct. 29, 2008, the entire contents of which are hereby incorporated by reference.

TECHNICAL FIELD

This invention relates to a novel silyl (meth)acrylate compound containing a siloxy group having a bulky substituent and its production method. This novel compound is useful as a material for a hydrolytic self-polishing polymer used for ship bottom paints and other applications.

BACKGROUND ART

A copolymer of tributyltin methacrylate with methyl methacrylate or the like has bee used for the hydrolytic self-polishing polymer in a ship bottom paint. This copolymer is hydrolyzed in water to release bistributyltin oxide, and the hydrolyzed part of the polymer turns into a carboxylic acid which is soluble in water, and therefore, this part dissolves in water to constantly expose an active surface.

However, the bistributyltin oxide released during the hydrolysis is highly toxic, and this compound pollutes the water into which it released. Accordingly, there is a growing concern for the adverse influence on the ecosystem.

Various tin-free polymers have been developed in view of such situation, and Japanese Patent No. 3053081 and U.S. Pat. No. 4,593,055 propose replacement of the bistributyltin methacrylate with a trialkylsilyl (meth)acrylate such as tributylsilyl methacrylate or triisopropylsilyl acrylate, and copolymerization of such trialkylsilyl (meth)acrylate with the alkyl methacrylate.

However, in the case of the copolymer of the trialkylsilyl (meth)acrylate and the alkyl methacrylate, the compound released by the self-polishing of the polymer by the hydrolysis is a trialkyl silanol which does not have the effect of suppressing the attachment of marine organisms, and also, the polymer itself does not have the effect of suppressing the attachment of marine organisms. Accordingly, and simultaneous use of a biocide is required to suppress the attachment of the marine organisms.

A hydrolytic self-polishing polymer which can do away with or reduce the biocide is disclosed in JP-A 63-253090. This polymer is prepared by using a siloxy group-containing silyl (meth)acrylate compound such as tris(trimethylsiloxy) silyl (meth)acrylate for the copolymerization with the alkyl methacrylate. This siloxy group-containing polymer has a reduced surface free energy, and this results in the reduced attachment of the marine organisms to the surface to allow prevention of the marine organism attachment with no or reduced amount of the biocide. This siloxy group-containing polymer also allows constant exposure of the active polymer surface by hydrolytic self-polishing of the polymer, and the attachment of the marine organisms is constantly suppressed. However, this siloxy group-containing silyl (meth)acrylate compound is hydrolyzed at an excessively high speed, and the anti-fouling effect was not sustainable due to the quick dissolution of the polymer. Accordingly, there is a demand for a siloxy group-containing silyl (meth)acrylate compound having a higher stability for the hydrolysis.

SUMMARY OF THE INVENTION

The present invention has been completed in view of the situation as described above, and an object of the present invention is to provide a silyl (meth)acrylate compound containing a siloxy group having a higher stability for hydrolysis. Another object of the present invention is to provide a method for its production.

The inventors of the present invention made an extensive study to realize the objects as described above, and found that a silyl (meth)acrylate compound containing a siloxy group having a bulky substituent introduced on the silicon atom to which the (meth)acryloyl group is bonded enjoys higher stability for hydrolysis compared to the siloxy group-containing silyl (meth)acrylate compound as described above. The present invention has been completed on the basis of such finding.

Accordingly, the present invention provides a silyl (meth) acrylate compound containing a siloxy group having a bulky substituent represented by the following general formula (1):

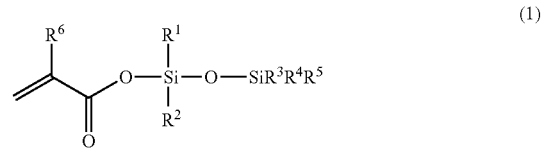

wherein $R^1$ and $R^2$ are independently a monovalent branched hydrocarbon group containing 3 to 10 carbon atoms having a hydrocarbon group at α or β position or a monovalent cyclic hydrocarbon group containing 3 to 10 carbon atoms; $R^3$, $R^4$, and $R^5$ are independently an unsubstituted or substituted hydrocarbon group containing 1 to 20 carbon atoms or a siloxy group represented by the following general formula (2):

wherein $R^7$, $R^8$, and $R^9$ are independently an unsubstituted or substituted hydrocarbon group containing 1 to 20 carbon atoms; and $R^6$ is hydrogen atom or methyl group.

The present invention also provides a method for producing the silyl (meth)acrylate compound containing a siloxy group having a bulky substituent represented by the above formula (1) comprising the step of reacting a chlorosilane compound containing a siloxy group having a bulky substituent represented by the following general formula (3):

wherein $R^1$ and $R^2$ are independently a monovalent branched hydrocarbon group containing 3 to 10 carbon atoms having a hydrocarbon group at α or β position or a monovalent cyclic hydrocarbon group containing 3 to 10 carbon atoms, and $R^3$, $R^4$, and $R^5$ are independently an unsubstituted or substituted hydrocarbon group containing 1 to 20 carbon atoms or a siloxy group represented by the following general formula (2):

wherein $R^7$, $R^8$, and $R^9$ are independently an unsubstituted or substituted hydrocarbon group containing 1 to 20 carbon atoms with acrylic acid or methacrylic acid in the presence of a basic compound.

Advantageous Effects of Invention

The silyl (meth)acrylate compound containing a siloxy group having a bulky substituent provided by the present invention is hydrolyzed at a reduced speed, and when this compound is copolymerized with an alkyl methacrylate, the resulting polymer is capable of suppressing attachment of marine organisms to the surface with no addition or with the addition of a minute amount of the biocide. Accordingly, this polymer is useful as a material for a hydrolytic self-polishing polymer used for the ship bottoms.

DETAILED DESCRIPTION OF THE INVENTION

Figure 1:
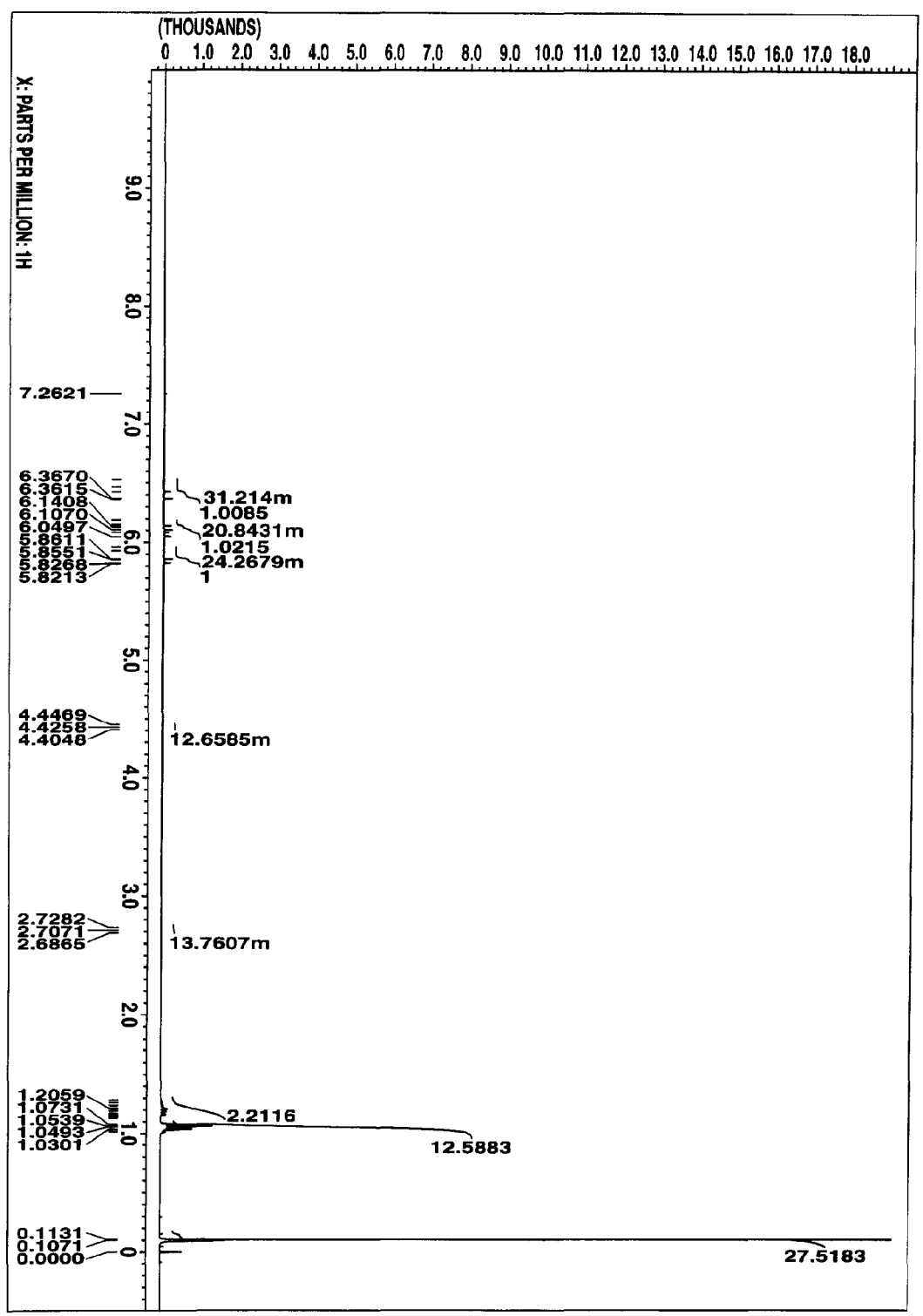
FIG. 1 is $^1$H-NMR spectrum of the 1-acryloyloxy-1,1-diisopropyl-3,3-bistrimethylsiloxy-trimethyltrisiloxane obtained in Example 1.

The silyl (meth)acrylate compound containing a siloxy group having a bulky substituent of the present invention is the compound represented by the following general formula (1):

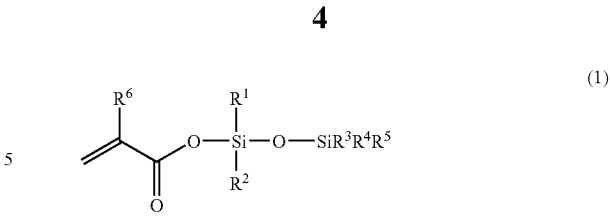

wherein $R^1$ and $R^2$ are independently a monovalent branched hydrocarbon group containing 3 to 10 carbon atoms having a hydrocarbon group at α or β position or a monovalent cyclic hydrocarbon group containing 3 to 10 carbon atoms; $R^3$, $R^4$, and $R^5$ are independently an unsubstituted or substituted hydrocarbon group containing 1 to 20 carbon atoms or a siloxy group represented by the following general formula (2):

wherein $R^7$, $R^8$, and $R^9$ are independently an unsubstituted or substituted hydrocarbon group containing 1 to 20 carbon atoms; and $R^6$ is hydrogen atom or methyl group.

The $R^1$ and $R^2$ which are independently a branched hydrocarbon group or a cyclic hydrocarbon group containing 3 to 10 carbon atoms are preferably a branched alkyl group or a cycloalkyl group, and exemplary such groups include isopropyl group, isobutyl group, sec-butyl group, 1-methylbutyl group, 1-ethylpropyl group, 2-ethylhexyl group, cyclopentyl group, and cyclohexyl group. The most preferred are isopropyl group and sec-butyl group.

The $R^3$, $R^4$, $R^5$, $R^7$, $R^8$, and $R^9$ which are independently an unsubstituted or substituted hydrocarbon group containing 1 to 20 carbon atoms are preferably an alkyl group such as methyl group, ethyl group, propyl group, isopropyl group, butyl group, isobutyl group, sec-butyl group, or t-butyl group; a cycloalkyl group such as cyclopentyl group or cyclohexyl group; an aryl group such as phenyl group; an aralkyl group such as benzyl group; an alkenyl group such as vinyl group or allyl group. $R^3$, $R^4$, and $R^5$ are preferably methyl group or trimethylsiloxy group.

Examples of the silyl (meth)acrylate compound containing a siloxy group having a bulky substituent represented by the general formula (1) include:
1-acryloyloxy-1,1-diisopropyl-trimethyldisiloxane,
1-acryloyloxy-1,1-diisopropyl-pentamethyltrisiloxane,
1-acryloyloxy-1,1-diisopropyl-3-trimethylsiloxy-tetramethyltrisiloxane,
1-acryloyloxy-1,1-diisopropyl-3,3-bistrimethylsiloxy-trimethyltrisiloxane,
1-acryloyloxy-1,1-di(sec-butyl)-trimethyldisiloxane,
1-acryloyloxy-1,1-di(sec-butyl)-pentamethyltrisiloxane,
1-acryloyloxy-1,1-di(sec-butyl)-3-trimethylsiloxy-tetramethyltrisiloxane,
1-acryloyloxy-1,1-di(sec-butyl)-3,3-bistrimethylsiloxy-trimethyltrisiloxane,
1-acryloyloxy-1,1-diisobutyl-trimethyldisiloxane,
1-acryloyloxy-1,1-diisobutyl-pentamethyltrisiloxane,
1-acryloyloxy-1,1-diisobutyl-3-trimethylsiloxy-tetramethyltrisiloxane,
1-acryloyloxy-1,1-diisobutyl-3,3-bistrimethylsiloxy-trimethyltrisiloxane,
1-acryloyloxy-1,1-diisopropyl-triethyldisiloxane,
1-acryloyloxy-1,1-diisopropyl-3,3-dimethyl-5,5,5-triethyl-trisiloxane,
1-acryloyloxy-1,1-diisopropyl-3-triethylsiloxy-tetramethyl-trisiloxane,
1-acryloyloxy-1,1-diisopropyl-3,3-bistriethylsiloxy-trimethyltrisiloxane, 1-acryloyloxy-1,1-di(sec-butyl)-triethyldisiloxane,
1-acryloyloxy-1,1-di(sec-butyl)-3,3-dimethyl-5,5,5-triethyltrisiloxane,
1-acryloyloxy-1,1-di(sec-butyl)-3-triethylsiloxy-tetramethyltrisiloxane,
1-acryloyloxy-1,1-di(sec-butyl)-3,3-bistriethylsiloxy-trimethyltrisiloxane,
1-acryloyloxy-1,1-diisobutyl-triethyldisiloxane,
1-acryloyloxy-1,1-diisobutyl-3,3-dimethyl-5,5,5-triethyltrisiloxane,
1-acryloyloxy-1,1-diisobutyl-3-triethylsiloxy-tetramethyltrisiloxane,
1-acryloyloxy-1,1-diisobutyl-3,3-bistriethylsiloxy-trimethyltrisiloxane,
1-acryloyloxy-1,1-diisopropyl-3-t-butyldimethyldisiloxane,
1-acryloyloxy-1,1-diisopropyl-5-t-butyltrimethyltrisiloxane,
1-acryloyloxy-1,1-diisopropyl-3-(t-butyldimethylsiloxy)-tetramethyltrisiloxane,
1-acryloyloxy-1,1-diisopropyl-3,3-bis(t-butyldimethylsiloxy)-trimethyltrisiloxane,
1-acryloyloxy-1,1-di(sec-butyl)-3-t-butyldimethyldisiloxane,
1-acryloyloxy-1,1-di(sec-butyl)-5-t-butyl-trimethyltrisiloxane,
1-acryloyloxy-1,1-di(sec-butyl)-3-(t-butyldimethylsiloxy)-tetramethyltrisiloxane,
1-acryloyloxy-1,1-di(sec-butyl)-3,3-bis(t-butyldimethyl-siloxy)-trimethyltrisiloxane,
1-acryloyloxy-1,1,3,3,3-pentaisopropyldisiloxane,
1-acryloyloxy-1,1,5,5,5-pentaisopropyl-dimethyltrisiloxane,
1-acryloyloxy-1,1-diisopropyl-3-(triisopropylsiloxy)-tetramethyltrisiloxane,
1-acryloyloxy-1,1-diisopropyl-3,3-bis(triisopropylsiloxy)-trimethyltrisiloxane,
1-acryloyloxy-1,1-di(sec-butyl)-3,3,3-triisopropyldisiloxane,
1-acryloyloxy-1,1-di(sec-butyl)-5,5,5-triisopropyldimethyltrisiloxane,
1-acryloyloxy-1,1-di(sec-butyl)-3-(triisopropylsiloxy)-tetramethyltrisiloxane,
1-acryloyloxy-1,1-di(sec-butyl)-3,3-bis(triisopropylsiloxy)-trimethyltrisiloxane,
1-acryloyloxy-1,1-diisobutyl-3,3,3-triisopropyldisiloxane,
1-acryloyloxy-1,1-diisobutyl-5,5,5-triisopropyldimethyltrisiloxane,
1-acryloyloxy-1,1-diisobutyl-3-(triisopropylsiloxy)-tetramethyltrisiloxane,
1-acryloyloxy-1,1-diisobutyl-3,3-bis(triisopropylsiloxy)-trimethyltrisiloxane,
1-methacryloyloxy-1,1-diisopropyl-trimethyldisiloxane,
1-methacryloyloxy-1,1-diisopropyl-pentamethyltrisiloxane,
1-methacryloyloxy-1,1-diisopropyl-3-trimethylsiloxy-tetramethyltrisiloxane,
1-methacryloyloxy-1,1-diisopropyl-3,3-bistrimethylsiloxy-trimethyltrisiloxane,
1-methacryloyloxy-1,1-di(sec-butyl)-trimethyldisiloxane,
1-methacryloyloxy-1,1-di(sec-butyl)-pentamethyltrisiloxane,
1-methacryloyloxy-1,1-di(sec-butyl)-3-trimethylsiloxy-tetramethyltrisiloxane,
1-methacryloyloxy-1,1-di(sec-butyl)-3,3-bistrimethylsiloxy-trimethyltrisiloxane,
1-methacryloyloxy-1,1-diisobutyl-trimethyldisiloxane,
1-methacryloyloxy-1,1-diisobutyl-pentamethyltrisiloxane,
1-methacryloyloxy-1,1-diisobutyl-3-trimethylsiloxy-tetramethyltrisiloxane,
1-methacryloyloxy-1,1-diisobutyl-3,3-bistrimethylsiloxy-trimethyltrisiloxane,
1-methacryloyloxy-1,1-diisopropyl-triethyldisiloxane,
1-methacryloyloxy-1,1-diisopropyl-3,3-dimethyl-5,5,5-triethyltrisiloxane,
1-methacryloyloxy-1,1-diisopropyl-3-triethylsiloxy-tetramethyltrisiloxane,
1-methacryloyloxy-1,1-diisopropyl-3,3-bistriethylsiloxy-trimethyltrisiloxane,
1-methacryloyloxy-1,1-di(sec-butyl)-triethyldisiloxane,
1-methacryloyloxy-1,1-di(sec-butyl)-3,3-dimethyl-5,5,5-triethyltrisiloxane,
1-methacryloyloxy-1,1-di(sec-butyl)-3-triethylsiloxy-tetramethyltrisiloxane,
1-methacryloyloxy-1,1-di(sec-butyl)-3,3-bistriethylsiloxy-trimethyltrisiloxane,
1-methacryloyloxy-1,1-diisobutyl-triethyldisiloxane,
1-methacryloyloxy-1,1-diisobutyl-3,3-dimethyl-5,5,5-triethyltrisiloxane,
1-methacryloyloxy-1,1-diisobutyl-3-triethylsiloxy-tetramethyltrisiloxane,
1-methacryloyloxy-1,1-diisobutyl-3,3-bistriethylsiloxy-trimethyltrisiloxane,
1-methacryloyloxy-1,1-diisopropyl-3-t-butyldimethyldisiloxane,
1-methacryloyloxy-1,1-diisopropyl-5-t-butyltrimethyl-trisiloxane,
1-methacryloyloxy-1,1-diisopropyl-3-(t-butyldimethylsiloxy)-tetramethyltrisiloxane,
1-methacryloyloxy-1,1-diisopropyl-3,3-bis(t-butyldimethyl-siloxy)-trimethyltrisiloxane,
1-methacryloyloxy-1,1-di(sec-butyl)-3-t-butyldimethyl-disiloxane,
1-methacryloyloxy-1,1-di(sec-butyl)-5-t-butyltrimethyl-trisiloxane,
1-methacryloyloxy-1,1-di(sec-butyl)-3-(t-butyldimethyl-siloxy)-tetramethyltrisiloxane,
1-methacryloyloxy-1,1-di(sec-butyl)-3,3-bis(t-butyldimethyl-siloxy)-trimethyltrisiloxane,
1-methacryloyloxy-1,1,3,3,3-pentaisopropyldisiloxane,
1-methacryloyloxy-1,1,5,5,5-pentaisopropyl-dimethyl-trisiloxane,
1-methacryloyloxy-1,1-diisopropyl-3-(triisopropylsiloxy)-tetramethyltrisiloxane,
1-methacryloyloxy-1,1-diisopropyl-3,3-bis(triisopropyl-siloxy)-trimethyltrisiloxane,
1-methacryloyloxy-1,1-di(sec-butyl)-3,3,3-triisopropyl-disiloxane,
1-methacryloyloxy-1,1-di(sec-butyl)-5,5,5-triisopropyl dimethyltrisiloxane,
1-methacryloyloxy-1,1-di(sec-butyl)-3-(triisopropylsiloxy)-tetramethyltrisiloxane,
1-methacryloyloxy-1,1-di(sec-butyl)-3,3-bis(triisopropyl-siloxy)-trimethyltrisiloxane,
1-methacryloyloxy-1,1-diisobutyl-3,3,3-triisopropyldisiloxane,
1-methacryloyloxy-1,1-diisobutyl-5,5,5-triisopropyldimethyl-trisiloxane,
1-methacryloyloxy-1,1-diisobutyl-3-(triisopropylsiloxy)-tetramethyltrisiloxane, and
1-methacryloyloxy-1,1-diisobutyl-3,3-bis(triisopropylsiloxy)-trimethyltrisiloxane.

An exemplary method for producing the silyl (meth)acrylate compound containing a siloxy group having a bulky substituent of the present invention represented by the general formula (1) is a method wherein a chlorosilane compound containing a siloxy group having a bulky substituent represented by the following general formula (3):

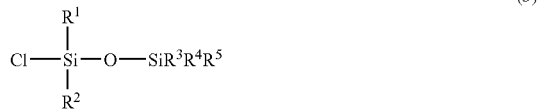

wherein $R^1$ and $R^2$ are independently a monovalent branched hydrocarbon group containing 3 to 10 carbon atoms having a hydrocarbon group at α or β position or a monovalent cyclic hydrocarbon group containing 3 to 10 carbon atoms, and $R^3$, $R^4$, and $R^5$ are independently an unsubstituted or substituted hydrocarbon group containing 1 to 20 carbon atoms or a siloxy group represented bfy the following general formula (2):

$$—OSiR^7R^8R^9 \quad (2)$$

wherein $R^7$, $R^8$, and $R^9$ are independently an unsubstituted or substituted hydrocarbon group containing 1 to 20 carbon atoms is reacted with acrylic acid or methacrylic acid in the presence of a basic compound.

Examples of the $R^1$, $R^2$ and $R^3$ to $R^9$ in the general formula (3) those as defined above.

Examples of the chlorosilane compound containing a siloxy group having a bulky substituent represented by the general formula (3) include
1-chloro-1,1-diisopropyl-trimethyldisiloxane,
1-chloro-1,1-diisopropyl-pentamethyltrisiloxane,
1-chloro-1,1-diisopropyl-3-trimethylsiloxy-tetramethyltrisiloxane,
1-chloro-1,1-diisopropyl-3,3-bistrimethylsiloxy-trimethyltrisiloxane,
1-chloro-1,1-di(sec-butyl)-trimethyldisiloxane,
1-chloro-1,1-di(sec-butyl)-pentamethyltrisiloxane,
1-chloro-1,1-di(sec-butyl)-3-trimethylsiloxy-tetramethyltrisiloxane,
1-chloro-1,1-di(sec-butyl)-3,3-bistrimethylsiloxy-trimethyltrisiloxane,
1-chloro-1,1-diisobutyl-trimethyldisiloxane,
1-chloro-1,1-diisobutyl-pentamethyltrisiloxane,
1-chloro-1,1-diisobutyl-3-trimethylsiloxy-tetramethyltrisiloxane,
1-chloro-1,1-diisobutyl-3,3-bistrimethylsiloxy-trimethyltrisiloxane,
1-chloro-1,1-diisopropyl-triethyldisiloxane,
1-chloro-1,1-diisopropyl-3,3-dimethyl-5,5,5-triethyltrisiloxane,
1-chloro-1,1-diisopropyl-3-triethylsiloxy-tetramethyltrisiloxane,
1-chloro-1,1-diisopropyl-3,3-bistriethylsiloxy-trimethyltrisiloxane,
1-chloro-1,1-di(sec-butyl)-triethyldisiloxane,
1-chloro-1,1-di(sec-butyl)-3,3-dimethyl-5,5,5-triethyltrisiloxane,
1-chloro-1,1-di(sec-butyl)-3-triethylsiloxy-tetramethyltrisiloxane,
1-chloro-1,1-di(sec-butyl)-3,3-bistriethylsiloxy-trimethyltrisiloxane,
1-chloro-1,1-diisobutyl-triethyldisiloxane,
1-chloro-1,1-diisobutyl-3,3-dimethyl-5,5,5-triethyltrisiloxane,
1-chloro-1,1-diisobutyl-3-triethylsiloxy-tetramethyltrisiloxane,
1-chloro-1,1-diisobutyl-3,3-bistriethylsiloxy-trimethyltrisiloxane,
1-chloro-1,1-diisopropyl-3-t-butyldimethyldisiloxane,
1-chloro-1,1-diisopropyl-5-t-butyltrimethyltrisiloxane,
1-chloro-1,1-diisopropyl-3-(t-butyldimethylsiloxy)-tetramethyltrisiloxane,
1-chloro-1,1-diisopropyl-3,3-bis(t-butyldimethylsiloxy)-trimethyltrisiloxane,
1-chloro-1,1-di(sec-butyl)-3-t-butyldimethyldisiloxane,
1-chloro-1,1-di(sec-butyl)-5-t-butyltrimethyltrisiloxane,
1-chloro-1,1-di(sec-butyl)-3-(t-butyldimethylsiloxy)-tetramethyltrisiloxane,
1-chloro-1,1-di(sec-butyl)-3,3-bis(t-butyldimethylsiloxy)-trimethyltrisiloxane,
1-chloro-1,1,3,3,3-pentaisopropyldisiloxane,
1-chloro-1,1,5,5,5-pentaisopropyl-dimethyltrisiloxane,
1-chloro-1,1-diisopropyl-3-(triisopropylsiloxy)-tetramethyltrisiloxane,
1-chloro-1,1-diisopropyl-3,3-bis(triisopropylsiloxy)-trimethyltrisiloxane,
1-chloro-1,1-di(sec-butyl)-3,3,3-triisopropyldisiloxane,
1-chloro-1,1-di(sec-butyl)-5,5,5-triisopropyldimethyl-trisiloxane,
1-chloro-1,1-di(sec-butyl)-3-(triisopropylsiloxy)-tetramethyltrisiloxane,
1-chloro-1,1-di(sec-butyl)-3,3-bis(triisopropylsiloxy)-trimethyltrisiloxane,
1-chloro-1,1-diisobutyl-3,3,3-triisopropyldisiloxane,
1-chloro-1,1-diisobutyl-5,5,5-triisopropyldimethyltrisiloxane,
1-chloro-1,1-diisobutyl-3-(triisopropylsiloxy)-tetramethyltrisiloxane, and
1-chloro-1,1-diisobutyl-3,3-bis(triisopropylsiloxy)-trimethyltrisiloxane.

The ratio of the acrylic acid or the methacrylic acid to the chlorosilane compound containing a siloxy group having a bulky substituent represented by the general formula (3) is not particularly limited. The acrylic acid or the methacrylic acid, however, is preferably used at an amount in the range of 0.5 to 2.0 mole, and in particular, at 0.8 to 1.2 mole per mole of the chlorosilane compound containing a siloxy group having a bulky substituent in view of the reactivity and the productivity.

In the reaction, the hydrochloric acid generated in the reaction is eliminated by using a basic compound. Exemplary basic compounds which may be used for the dehydrochlorination include trimethylamine, triethylamine, tripropylamine, tributylamine, ethyl diisopropylamine, pyridine, dimethylaminopyridine, dimethylaniline, methyl imidazole, tetramethylethylenediamine, 1,8-diazabicyclo[5.4.0]undecene-7, ammonia, imidazole, sodium hydrogencarbonate, sodium carbonate, sodium methoxide, and sodium ethoxide.

Amount of the basic compound added is not particularly limited. The basic compound, however, is preferably added at an amount in the range of 0.5 to 2.0 mole, and in particular, at 0.8 to 1.5 mole per mole of the acrylic acid or the methacrylic acid in view of the reactivity and the productivity. When the basic compound is used at an amount less than 0.5 mole, the reaction may not be sufficiently completed due to the insufficient dehydrochlorination, whereas addition in excess of 2.0 mole may result in the reaction promotion not consistent with the amount of the basic compound added.

In the reaction as described above, a phase transfer catalyst may be used for the purpose of the reaction promotion. Exemplary phase transfer catalysts include quaternary ammonium salt, quaternary phosphonium salts, and crown ethers, and the preferred are quaternary ammonium salts in view of industrial availability and low cost.

Examples of such quaternary ammonium salts include tetramethylammonium chloride, tetramethylammonium bromide, tetraethylammonium chloride, tetraethylammonium bromide, tetrapropylammonium chloride, tetrapropylammonium bromide, tetrabutylammonium chloride, tetrabutylammonium bromide, trioctylmethylammonium chloride, trioctylmethylammonium bromide, benzyltrimethylammonium chloride, benzyltrimethylammonium bromide, cetyltrimethylammonium chloride, and cetyltrimethylammonium bromide.

The amount of the phase transfer catalyst used is not particularly limited. The phase transfer catalyst, however, is preferably used at an amount of 0.0001 to 0.1 mole, and in particular, 0.001 to 0.05 mole per mole of the acrylic acid or the methacrylic acid in view of the reactivity and the productivity.

The reaction temperature is not particularly limited. The reaction, however, is preferably conducted at normal pressure or a higher pressure at a temperature of −20° C. to 200° C., and more preferably at 0° C. to 150° C.

This reaction can proceed without any solvent, however, the reaction can be promoted in the presence of a solvent. Exemplary solvents which may be used in this reaction include hydrocarbon solvents such as pentane, hexane, cyclohexane, isooctane, benzene, toluene, and xylene, ether solvents such as diethylether, tetrahydrofuran, and dioxane, ester solvents such as ethyl acetate and butyl acetate, ketone solvents such as acetone, methyl ethyl ketone, and methyl isobutyl ketone, aprotic polar solvents such as acetonitrile, dimethyl sulfoxide, N,N-dimethylformamide, N-methylpyrrolidone, and hexamethylphosphoric triamide, and chlorinated hydrocarbon solvents such as dichloromethane and chloroform, which may be used alone or in combination of two or more.

In the reaction as described above, a polymerization inhibitor may be added to prevent the polymerization. Exemplary polymerization inhibitors include hydroquinone, p-methoxyphenol, and 2,6-di-tert-butylphenol, and 2,6-di-tert-butyl-4-methylphenol.

Hydrochloride of the amine compound will be left after the reaction, and this hydrochloride can be removed by filtration, or by addition of water, ethylenediamine, 1,8-diazabicyclo[5.4.0]undecene-7, or the like followed by separation. The target product may be collected from the mixture after the removal of the hydrochloride by a distillation or other method commonly used in the art.

EXAMPLES

Next, the present invention is described in further detail by referring to Examples and Experimental Examples which by no means limit the scope of the present invention.

Example 1

Synthesis of 1-acryloyloxy-1,1-diisopropyl-3,3-bistrimethylsiloxy-trimethyltrisiloxane A flask equipped with a stirrer, a reflux condenser, a dropping funnel, and a thermometer was charged with 1-chloro-1,1-diisopropyl-3,3-bistrimethylsiloxy-trimethyltrisiloxane (46.1 g, 0.1 mol), triethylamine (11.1 g, 0.11 mol), toluene (30 ml), and 2,6-di-tert-butyl-4-methyl phenol (0.05 g), and acrylic acid (7.6 g, 0.105 mol) was added dropwise at room temperature for 1 hour, and stirring was continued for 2 hours. The hydrochloride formed was removed by filtration, and the reaction mixture was distilled to obtain 38.6 g of a fraction having a boiling point of 132° C. at 0.4 kPa.

Figure 2:
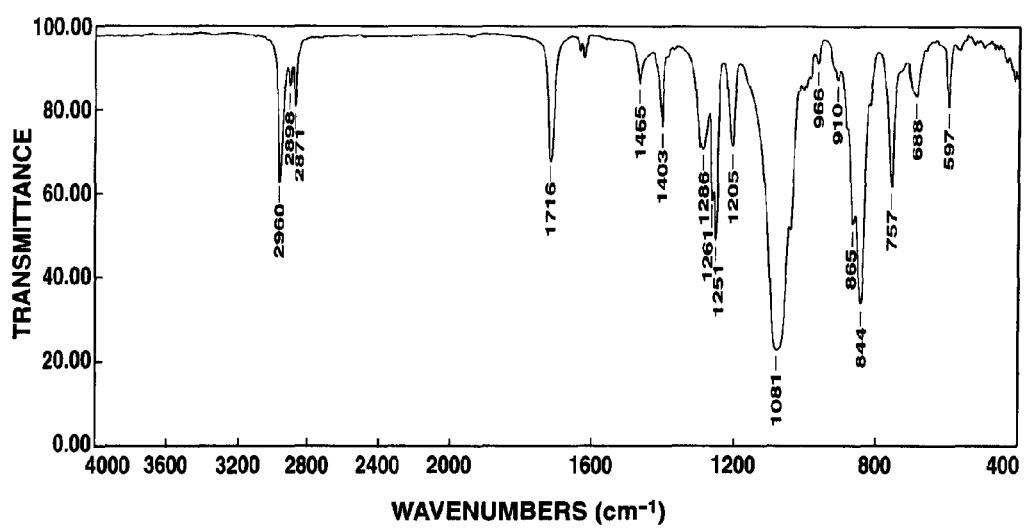
FIG. 2 is IR spectrum of the 1-acryloyloxy-1,1-diisopropyl-3,3-bistrimethylsiloxy-trimethyltrisiloxane obtained in Example 1.

The resulting fraction was evaluated for $^1$H-NMR spectrum (deuterated chloroform solvent) and IR spectrum.
Mass spectrum:
m/z 481, 453, 267, 73, 55
$^1$H-NMR spectrum (deuterated chloroform solvent):
FIG. 1 is the chart for the $^1$H-NMR spectrum
IR spectrum:
FIG. 2 is the chart for the IR spectrum
These results confirmed that the resulting compound was 1-acryloyloxy-1,1-diisopropyl-3,3-bistrimethylsiloxy-trimethyltrisiloxane.

Example 2

Synthesis of 1-methacryloyloxy-1,1-diisopropyl-3,3-bistrimethylsiloxy-trimethyltrisiloxane A flask equipped with a stirrer, a reflux condenser, a dropping funnel, and a thermometer was charged with 1-chloro-1,1-diisopropyl-3,3-bistrimethylsiloxy-trimethyltrisiloxane (46.1 g, 0.1 mol), triethylamine (11.1 g, 0.11 mol), toluene (30 ml), and 2,6-di-tert-butyl-4-methyl phenol (0.05 g), and methacrylic acid (9.0 g, 0.105 mol) was added dropwise at room temperature for 1 hour, and stirring was continued for 2 hours. The hydrochloride formed was removed by filtration, and the reaction mixture was distilled to obtain 43.7 g of a fraction having a boiling point of 105-108° C. at 30 kPa.

Figure 3:
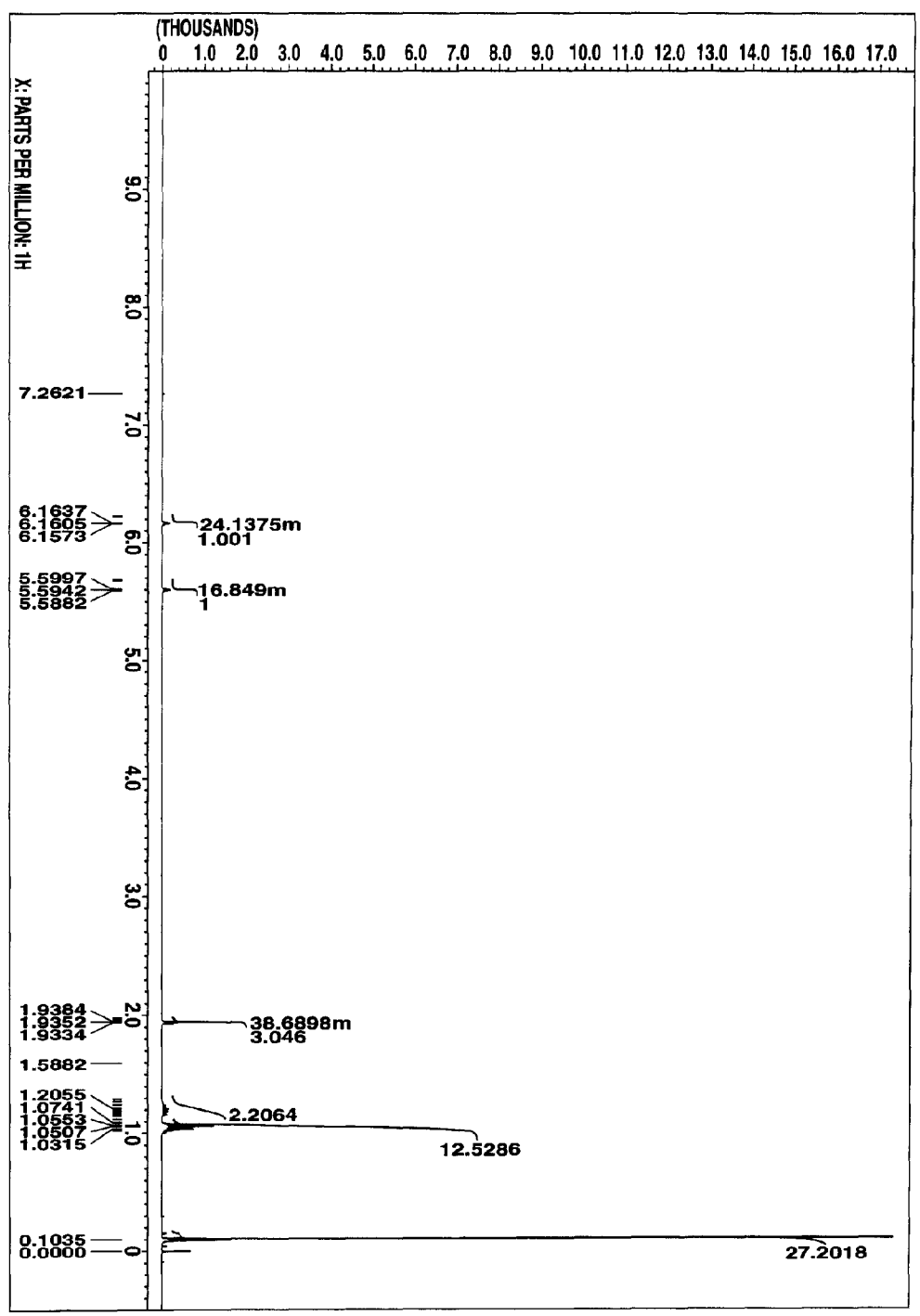
FIG. 3 is $^1$H-NMR spectrum of the 1-methacryloyloxy-1,1-diisopropyl-3,3-bistrimethylsiloxy-trimethyltrisiloxane obtained in Example 2.
Figure 4:
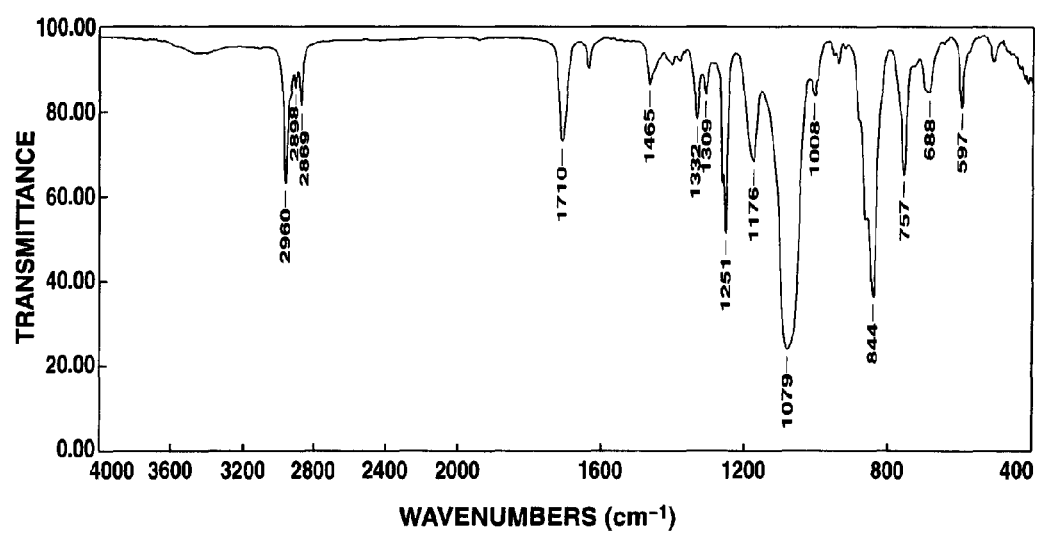
FIG. 4 is IR spectrum of the 1-methacryloyloxy-1,1-diisopropyl-3,3-bistrimethylsiloxy-trimethyltrisiloxane obtained in Example 2.

The resulting fraction was evaluated for $^1$H-NMR spectrum (deuterated chloroform solvent) and IR spectrum.
Mass spectrum:
m/z 495, 467, 267, 73, 69, 41
$^1$H-NMR spectrum (deuterated chloroform solvent):
FIG. 3 is the chart for the $^1$H-NMR spectrum
IR spectrum:
FIG. 4 is the chart for the $^I$R spectrum
These results confirmed that the resulting compound was 1-methacryloyloxy-1,1-diisopropyl-3,3-bistrimethylsiloxy-trimethyltrisiloxane.

Example 3

Synthesis of 1-acryloyloxy-1,1-di(sec-butyl)-3,3-bistrimethylsiloxy-trimethyltrisiloxane A flask equipped with a stirrer, a reflux condenser, a dropping funnel, and a thermometer was charged with 1-chloro-1,1-di(sec-butyl)-3,3-bistrimethylsiloxy-trimethyltrisiloxane (48.9 g, 0.1 mol), triethylamine (11.1 g, 0.11 mol), toluene (30 ml), and 2,6-di-tert-butyl-4-methyl phenol (0.05 g), and acrylic acid (7.6 g, 0.105 mol) was added dropwise at room temperature for 1 hour, and stirring was continued for 2 hours. The hydrochloride formed was removed by filtration, and the reaction mixture was distilled to obtain 43.5 g of a fraction having a boiling point of 147-148° C. at 0.3 kPa.

Figure 5:
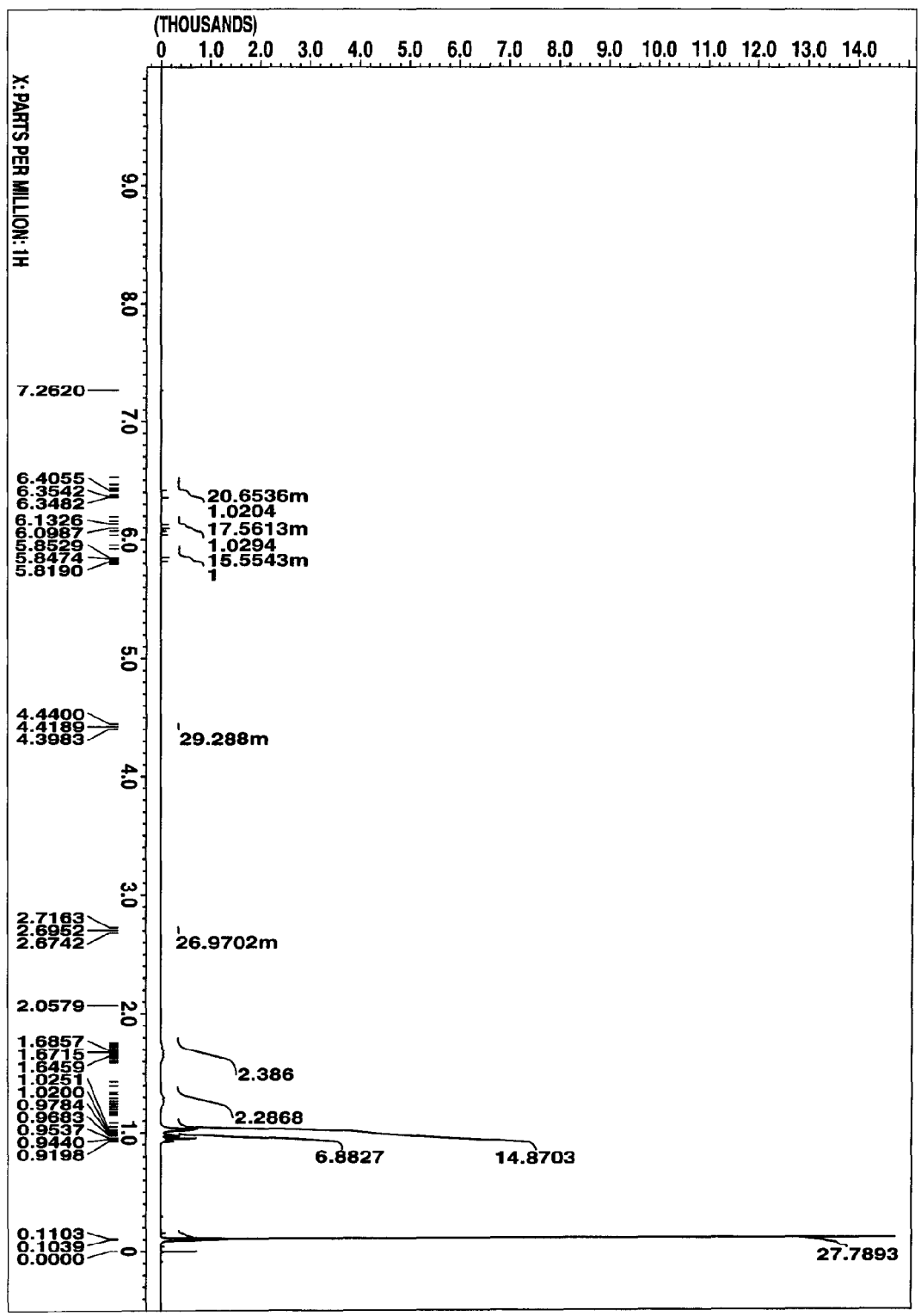
FIG. 5 is $^1$H-NMR spectrum of the 1-acryloyloxy-1,1-di(sec-butyl)-3,3-bistrimethylsiloxy-trimethyltrisiloxane obtained in Example 3.
Figure 6:
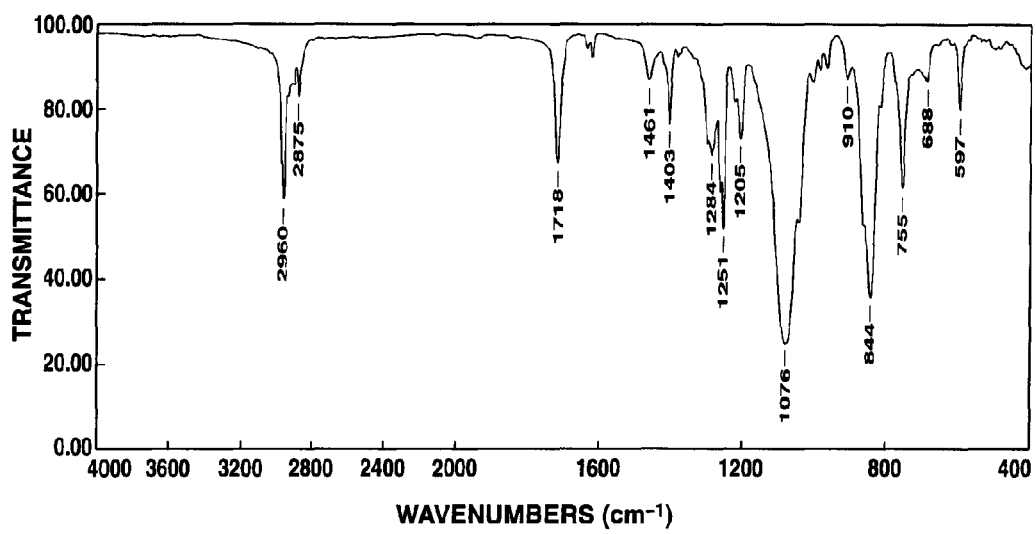
FIG. 6 is IR spectrum of the 1-acryloyloxy-1,1-di(sec-butyl)-3,3-bistrimethylsiloxy-trimethyltrisiloxane obtained in Example 3.

The resulting fraction was evaluated for $^1$H-NMR spectrum (deuterated chloroform solvent) and IR spectrum.
Mass spectrum:
m/z 509, 467, 267, 73, 55
$^1$H-NMR spectrum (deuterated chloroform solvent):
FIG. 5 is the chart for the $^1$H-NMR spectrum
IR spectrum:
FIG. 6 is the chart for the IR spectrum
These results confirmed that the resulting compound was 1-acryloyloxy-1,1-di(sec-butyl)-3,3-bistrimethylsiloxy-trimethyltrisiloxane.

Example 4

Synthesis of 1-methacryloyloxy-1,1-di(sec-butyl)-3,3-bistrimethylsiloxy-trimethyltrisiloxane A flask equipped with a stirrer, a reflux condenser, a dropping funnel, and a thermometer was charged with 1-chloro-1,1-di(sec-butyl)-3,3-bistrimethylsiloxy-trimethyltrisiloxane (48.9 g, 0.1 mol), triethylamine (11.1 g, 0.11 mol), toluene (30 ml), and 2,6-di-tert-butyl-4-methyl phenol (0.05 g), and methacrylic acid (9.0 g, 0.105 mol) was added dropwise at room temperature for 1 hour, and stirring was continued for 2 hours. The hydrochloride formed was removed by filtration, and the reaction mixture was distilled to obtain 39.5 g of a fraction having a boiling point of 150° C. at 0.3 kPa.

The resulting fraction was evaluated for $^1$H-NMR spectrum (deuterated chloroform solvent) and IR spectrum.

Figure 7:
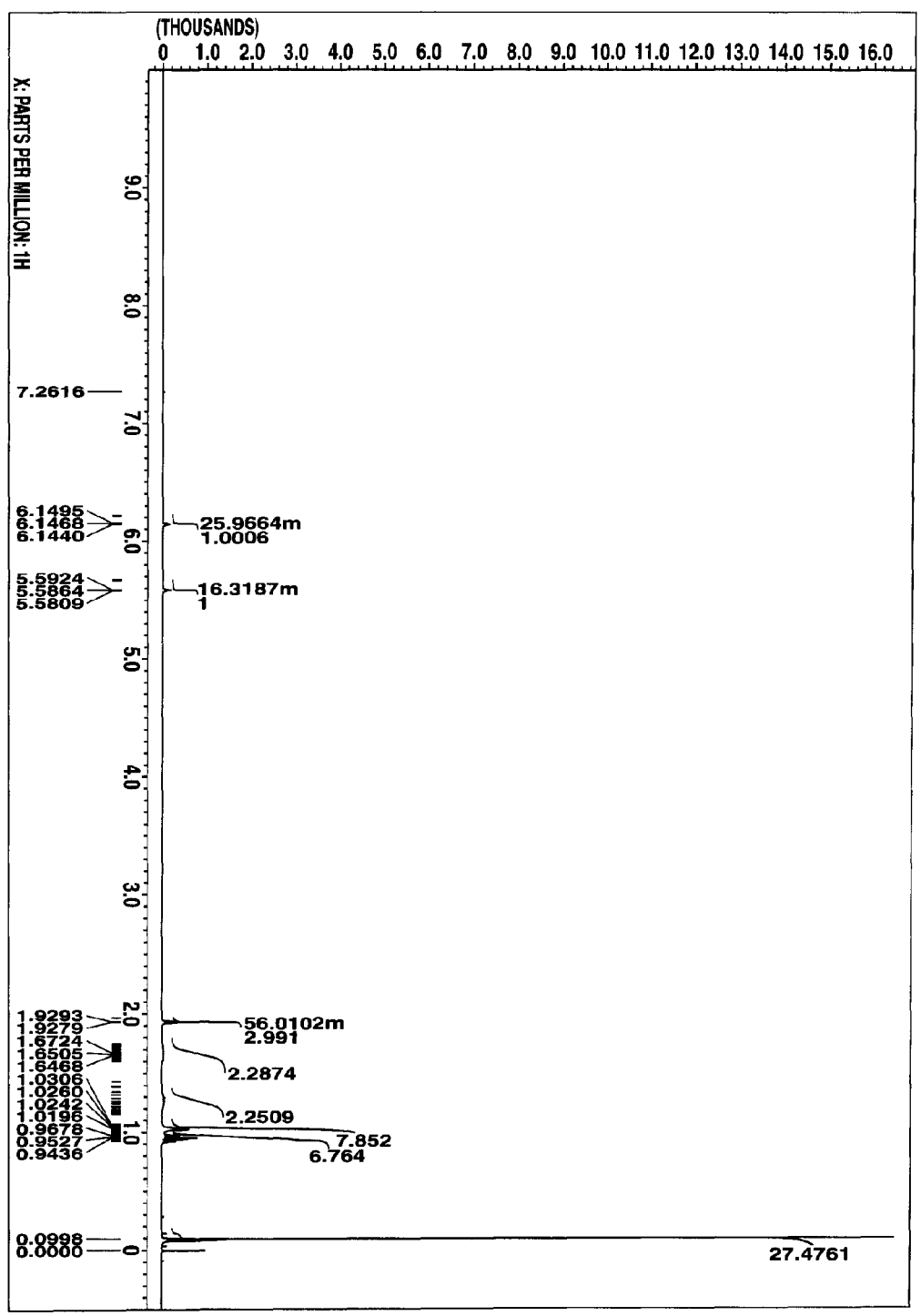
FIG. 7 is $^1$H-NMR spectrum of the 1-methacryloyloxy-1,1-di(sec-butyl)-3,3-bistrimethylsiloxy-trimethyltrisiloxane obtained in Example 4.
Figure 8:
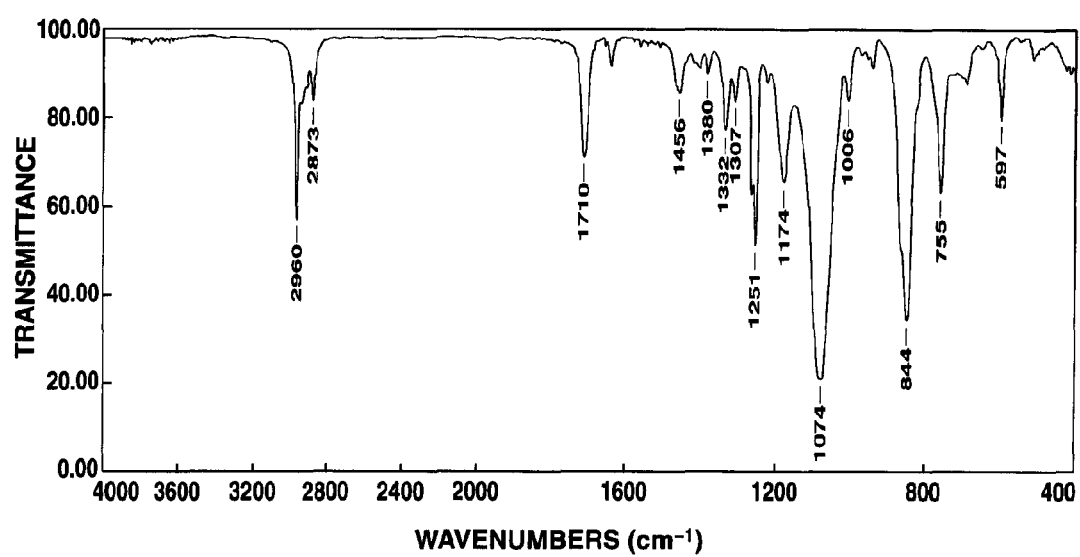
FIG. 8 is IR spectrum of the 1-methacryloyloxy-1,1-di(sec-butyl)-3,3-bistrimethylsiloxy-trimethyltrisiloxane obtained in Example 4.

Mass spectrum:
m/z 523, 481, 267, 73, 69, 41
$^1$H-NMR spectrum (deuterated chloroform solvent):
FIG. 7 is the chart for the $^1$H-NMR spectrum
IR spectrum:
FIG. 8 is the chart for the IR spectrum These results confirmed that the resulting compound was 1-methacryloyloxy-1,1-di(sec-butyl)-3,3-bistrimethyl-siloxy-trimethyltrisiloxane.

Example 5

Synthesis of 1-acryloyloxy-1,1-diisopropyl-3-trimethylsiloxy-tetramethyltrisiloxane A flask equipped with a stirrer, a reflux condenser, a dropping funnel, and a thermometer was charged with 1-chloro-1,1-diisopropyl-3-trimethylsiloxy-tetramethyl-trisiloxane (38.7 g, 0.1 mol), triethylamine (11.1 g, 0.11 mol), toluene (30 ml), and 2,6-di-tert-butyl-4-methyl phenol (0.04 g), and acrylic acid (7.6 g, 0.105 mol) was added dropwise at room temperature for 1 hour, and stirring was continued for 2 hours. The hydrochloride formed was removed by filtration, and the reaction mixture was distilled to obtain 36.1 g of a fraction having a boiling point of 120° C. at 0.3 kPa.

The resulting fraction was evaluated for $^1$H-NMR spectrum (deuterated chloroform solvent) and IR spectrum.

Figure 9:
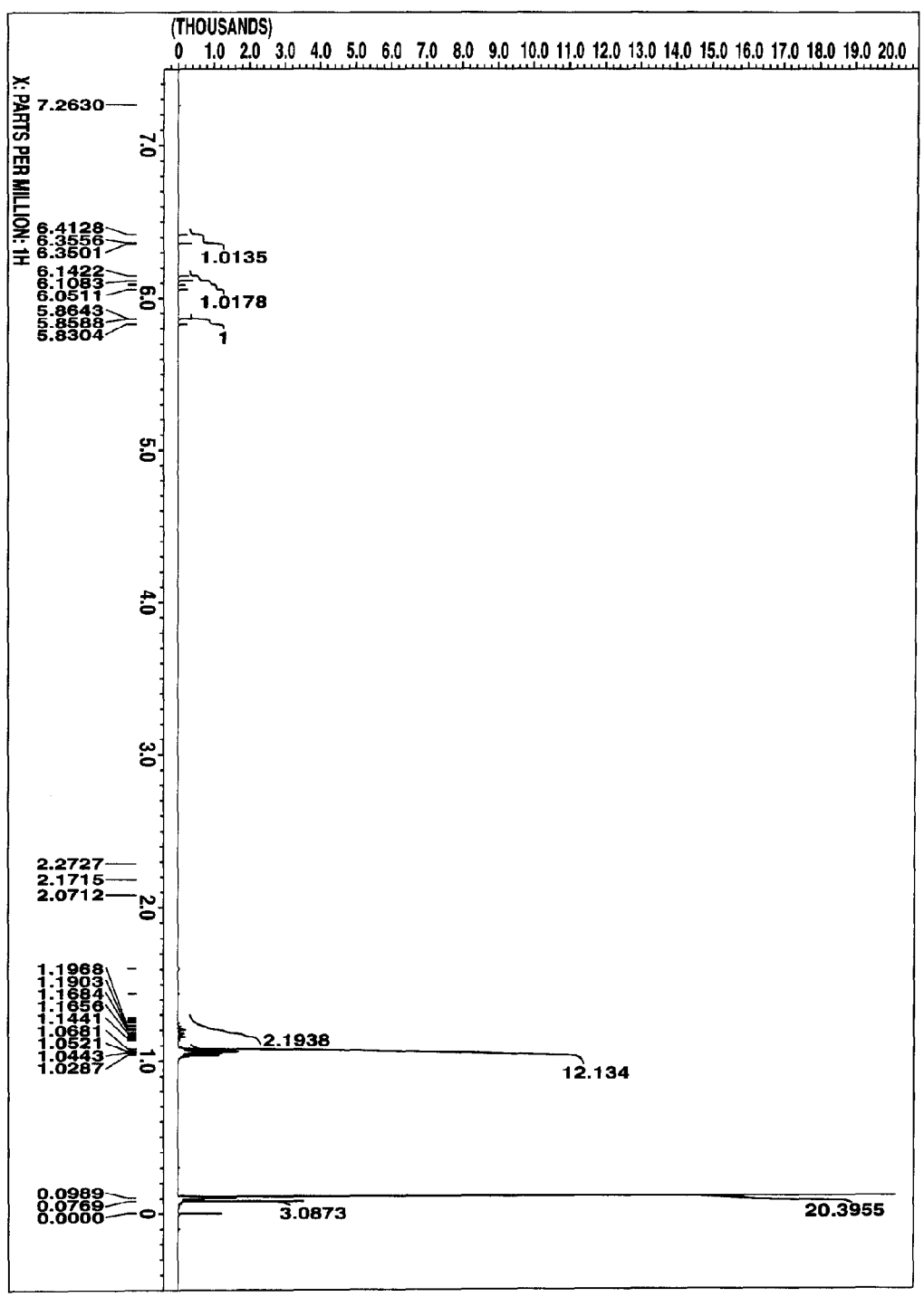
FIG. 9 is $^1$H-NMR spectrum of the 1-acryloyloxy-1,1-diisopropyl-3-trimethylsiloxy-tetramethyltrisiloxane obtained in Example 5.
Figure 10:
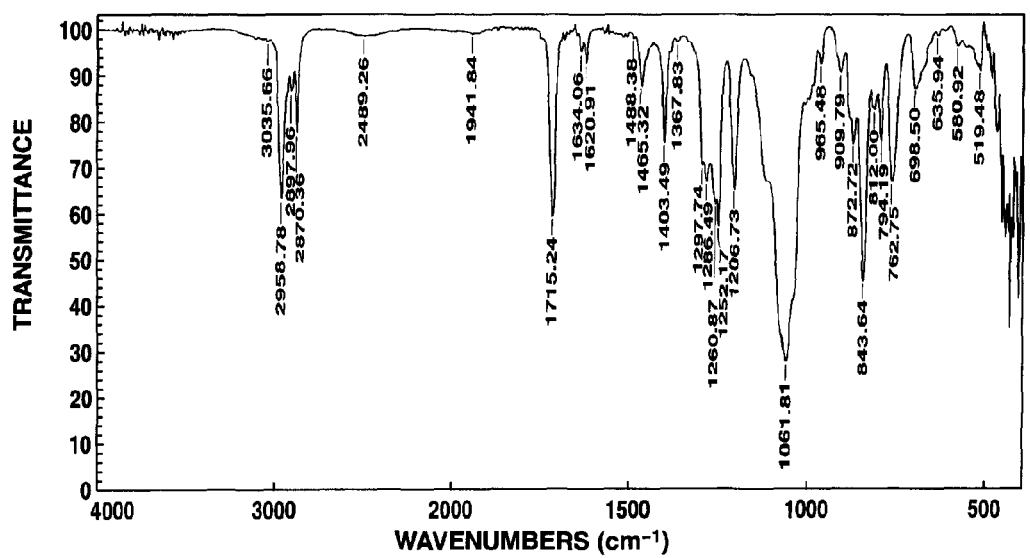
FIG. 10 is IR spectrum of the 1-acryloyloxy-1,1-diisopropyl-3-trimethylsiloxy-tetramethyltrisiloxane obtained in Example 5.

Mass spectrum:
m/z 407, 379, 281, 73, 55
$^1$H-NMR spectrum (deuterated chloroform solvent):
FIG. 9 is the chart for the $^1$H-NMR spectrum
IR spectrum:
FIG. 10 is the chart for the IR spectrum These results confirmed that the resulting compound was 1-acryloyloxy-1,1-diisopropyl-3-trimethylsiloxy-tetramethyltrisiloxane.

Example 6

Synthesis of 1-acryloyloxy-1,1-diisopropyl-pentamethyltrisiloxane

A flask equipped with a stirrer, a reflux condenser, a dropping funnel, and a thermometer was charged with 1-chloro-1,1-diisopropyl-pentamethyltrisiloxane (31.3 g, 0.1 mol), triethylamine (11.1 g, 0.11 mol), toluene (30 ml), 2,6-di-tert-butyl-4-methyl phenol (0.04 g), and acrylic acid (7.6 g, 0.105 mol) was added dropwise at room temperature for 1 hour, and stirring was continued for 2 hours. The hydrochloride formed was removed by filtration, and the reaction mixture was distilled to obtain 27.4 g of a fraction having a boiling point of 103° C. at 0.4 kPa.

The resulting fraction was evaluated for $^1$H-NMR spectrum (deuterated chloroform solvent) and IR spectrum.

Figure 11:
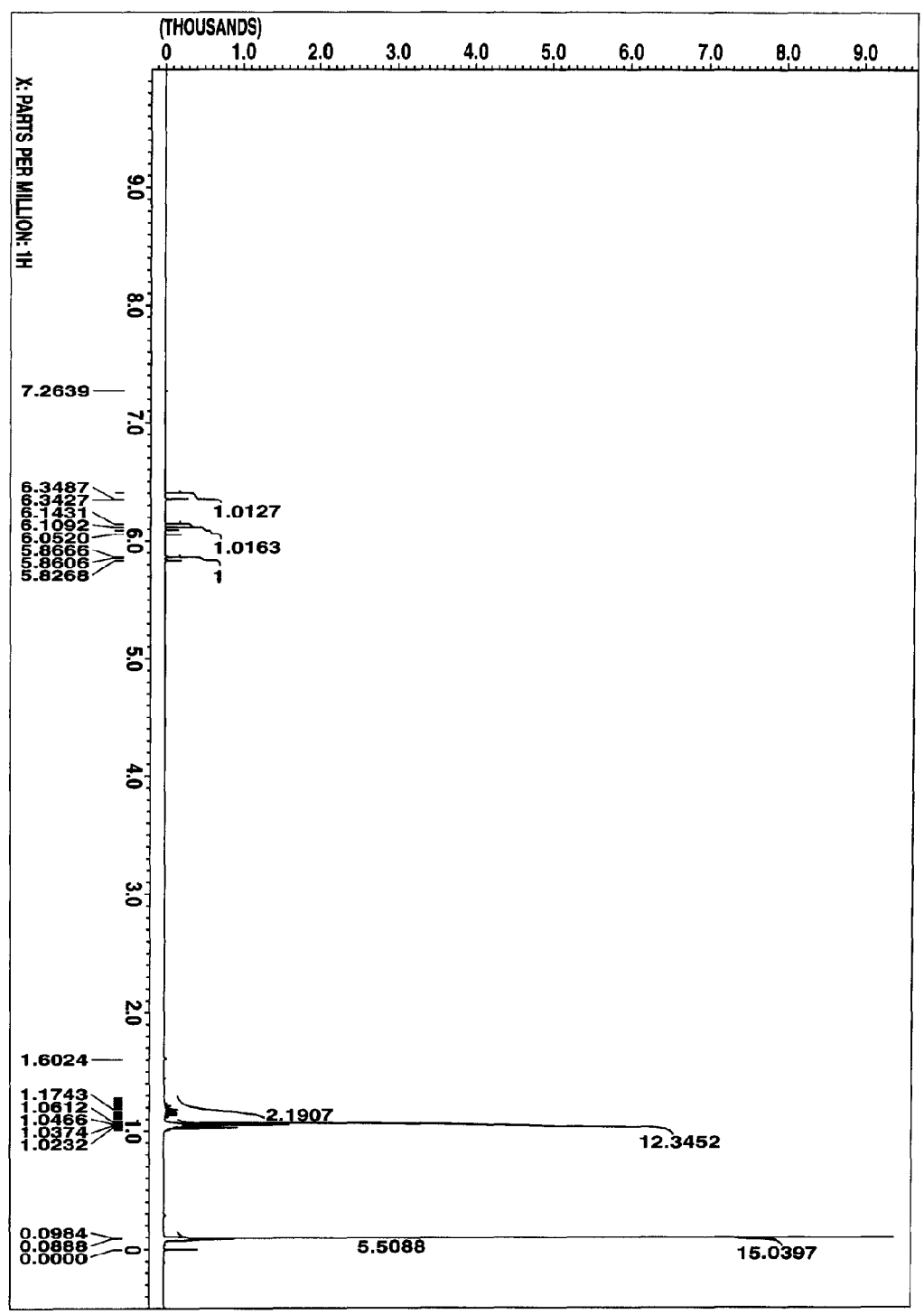
FIG. 11 is $^1$H-NMR spectrum of the 1-acryloyloxy-1,1-diisopropyl-pentamethyltrisiloxane obtained in Example 6.
Figure 12:
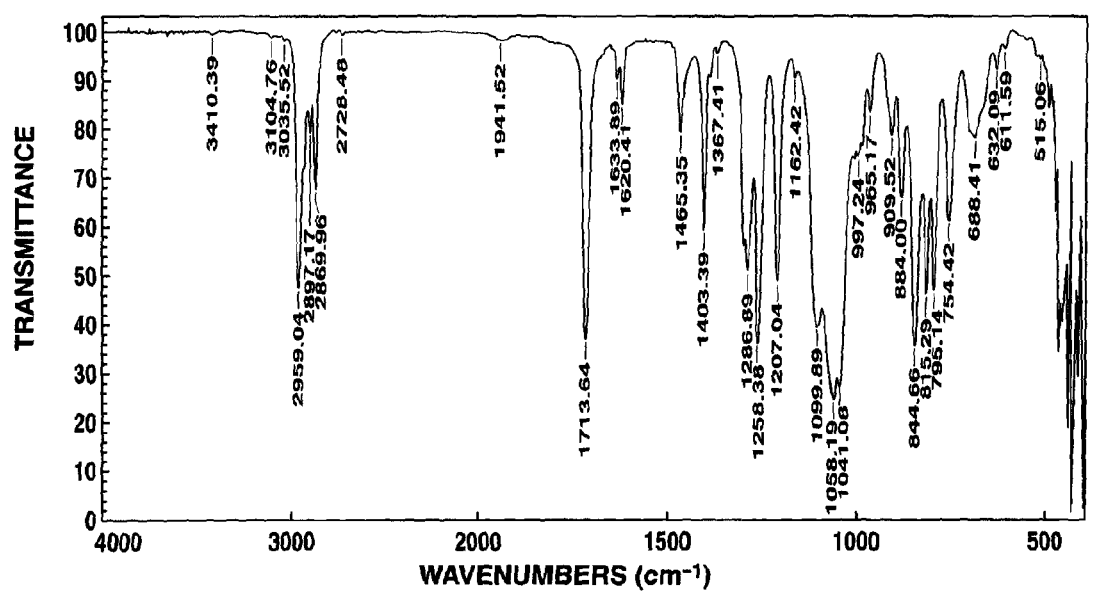
FIG. 12 is IR spectrum of the 1-acryloyloxy-1,1-diisopropyl-pentamethyltrisiloxane obtained in Example 6.

Mass spectrum:
m/z 333, 305, 207, 73, 55
$^1$H-NMR spectrum (deuterated chloroform solvent):
FIG. 11 is the chart for the $^1$H-NMR spectrum
IR spectrum:
FIG. 12 is the chart for the IR spectrum These results confirmed that the resulting compound was 1-acryloyloxy-1,1-diisopropyl-pentamethyltrisiloxane.

Example 7

Synthesis of 1-acryloyloxy-1,1-diisopropyl-trimethyldisiloxane

A flask equipped with a stirrer, a reflux condenser, a dropping funnel, and a thermometer was charged with 1-chloro-1,1-diisopropyl-trimethyldisiloxane (47.8 g, 0.2 mol), triethylamine (22.3 g, 0.22 mol), toluene (60 ml), 2,6-di-tert-butyl-4-methyl phenol (0.06 g), and acrylic acid (15.1 g, 0.21 mol) was added dropwise at room temperature for 1 hour, and stirring was continued for 2 hours. The hydrochloride formed was removed by filtration, and the reaction mixture was distilled to obtain 46.3 g of a fraction having a boiling point of 82° C. at 0.4 kPa.

The resulting fraction was evaluated for $^1$H-NMR spectrum (deuterated chloroform solvent) and IR spectrum.

Figure 13:
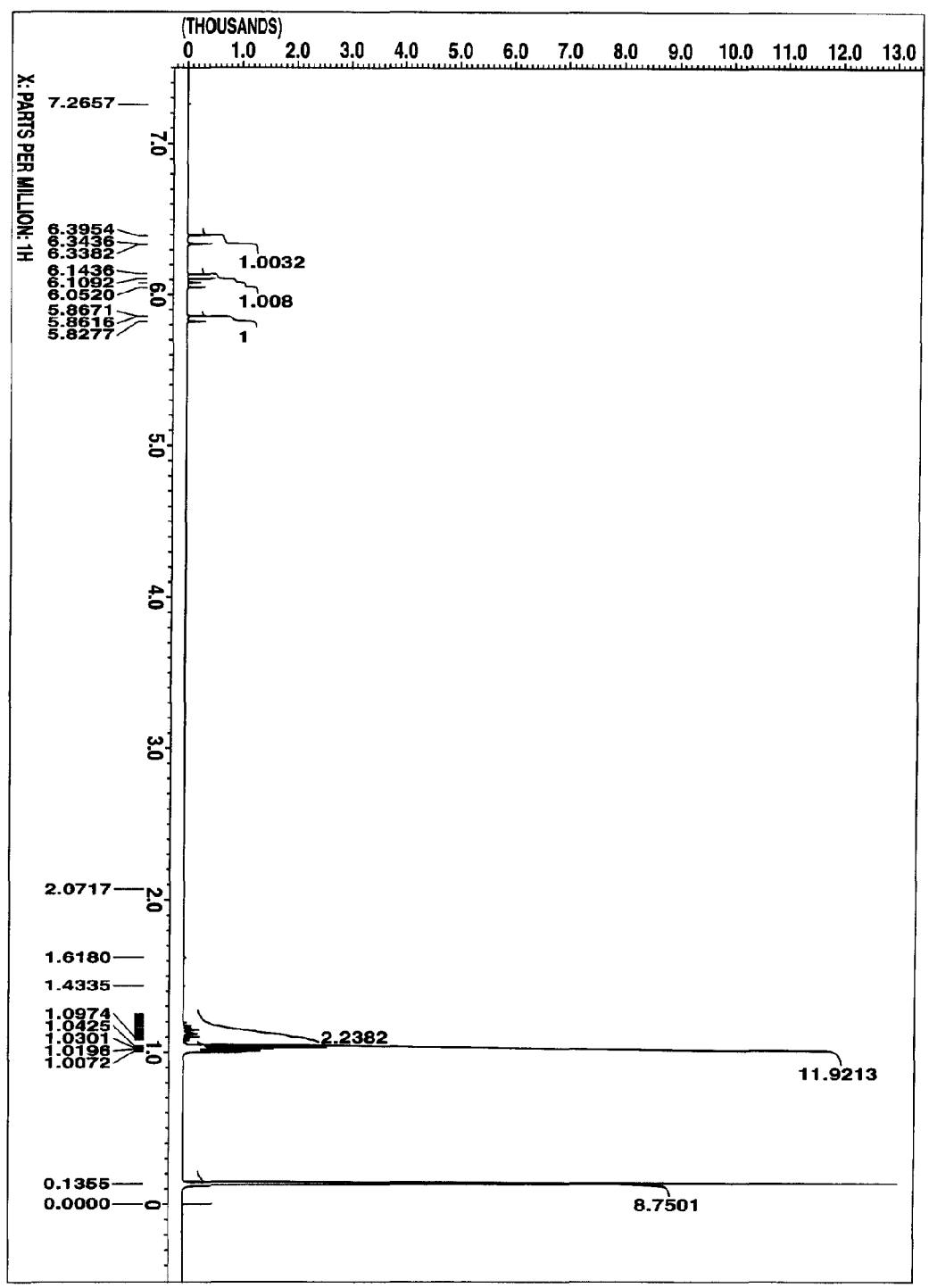
FIG. 13 is $^1$H-NMR spectrum of the 1-acryloyloxy-1,1-diisopropyl-trimethyldisiloxane obtained in Example 7.
Figure 14:
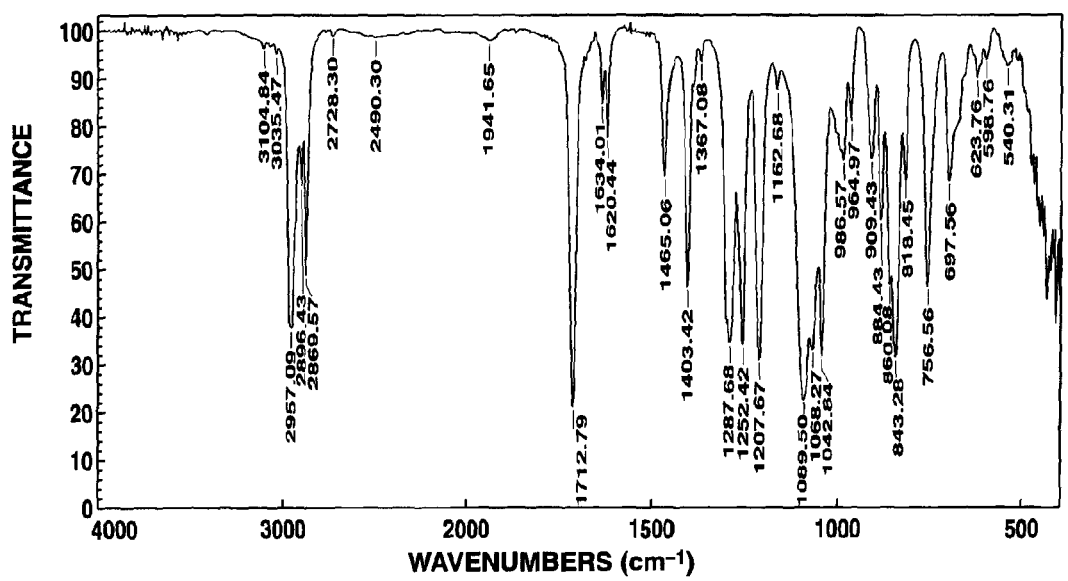
FIG. 14 is IR spectrum of the 1-acryloyloxy-1,1-diisopropyl-trimethyldisiloxane obtained in Example 7.

Mass spectrum:
m/z 259, 231, 133, 73, 55
$^1$H-NMR spectrum (deuterated chloroform solvent):
FIG. 13 is the chart for the $^1$H-NMR spectrum
IR spectrum:
FIG. 14 is the chart for the IR spectrum These results confirmed that the resulting compound was 1-acryloyloxy-1,1-diisopropyl-trimethyldisiloxane.

Next, Experimental Examples are shown, in which "%" means "% by weight".

Experimental Example 1

Comparison of hydrolyzability between 1-acryloyloxy-1,1-diisopropyl-3,3-bistrimethylsiloxy-trimethyltrisiloxane and tris(trimethylsiloxy)silyl acrylate A flask equipped with a stirrer, a reflux condenser, and a thermometer was charged with water (0.5 g), tetrahydrofuran (7.5 g), 1-acryloyloxy-1,1-diisopropyl-3,3-bistrimethylsiloxy-trimethyltrisiloxane (2.5 g, 0.005 mol), tris(trimethylsiloxy)silyl acrylate (1.8 g, 0.005 mol), and xylene (1 g, as an internal reference), and the mixture was stirred at room temperature. After 3 hours, degree of the hydrolysis of the siloxy group-containing silyl acrylates was analyzed by gas chromatography to find that, while percentage of the 1-acryloyloxy-1,1-diiso-propyl-3,3-bistrimethylsiloxy-trimethyltrisiloxane that was hydrolyzed into the acrylic acid and 1-hydroxy-1,1-diisopropyl-3,3-bistrimethylsiloxy-trimethyltrisiloxane was only 2%, percentage of the tris(trimethylsiloxy)silyl acrylate that was hydrolyzed into the acrylic acid and tris(trimethylsiloxy) silanol was 10%. This demonstrated the higher stability to hydrolysis of the 1-acryloyloxy-1,1-diisopropyl-3,3-bistrimethylsiloxy-trimethyltrisiloxane compared to the tris(trimethylsiloxy)-silyl acrylate.

Experimental Example 2

Comparison of hydrolyzability between 1-acryloyloxy-1,1-di(sec-butyl)-3,3-bistrimethylsiloxy-trimethyltrisiloxane and tris(trimethylsiloxy)silyl acrylate A flask equipped with a stirrer, a reflux condenser, and a thermometer was charged with water (0.5 g), tetrahydrofuran (7.5 g), 1-acryloyloxy-1,1-di(sec-butyl)-3,3-bistrimethylsiloxy-trimethyltrisiloxane (2.6 g, 0.005 mol), tris(trimethylsiloxy)silyl acrylate (1.8 g, 0.005 mol), and xylene (1 g, as an internal reference), and the mixture was stirred at room temperature. After 3 hours, degree of the hydrolysis of the siloxy group-containing silyl acrylates was analyzed by gas chromatography to find that, while percentage of the 1-acryloyloxy-1,1-di(sec-butyl)-3,3-bistrimethylsiloxy-trimethyltrisiloxane that was hydrolyzed into the acrylic acid and 1-hydroxy-1,1-di(sec-butyl)-3,3-bistrimethylsiloxy-trimethyltrisiloxane was only 2%, percentage of the tris(trimethylsiloxy)silyl acrylate that was hydrolyzed into the acrylic acid and tris(trimethylsiloxy) silanol was 10%. This demonstrated the higher stability to hydrolysis of the 1-acryloyloxy-1,1-di(sec-butyl)-3,3-bistrimethylsiloxy-trimethyltrisiloxane compared to the tris(trimethylsiloxy)silyl acrylate.

Japanese Patent Application No. 2008-278151 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A silyl (meth)acrylate compound containing a siloxy group having a bulky substituent represented by the following general formula (1):

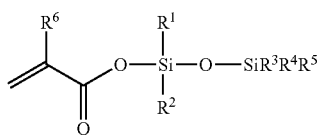
(1)

wherein $R^1$ and $R^2$ are independently a monovalent branched hydrocarbon group containing 3 to 10 carbon atoms having a hydrocarbon group at α or β position or a monovalent cyclic hydrocarbon group containing 3 to 10 carbon atoms; $R^3$, $R^4$, and $R^5$ are independently an unsubstituted or substituted hydrocarbon group containing 1 to 20 carbon atoms or a siloxy group represented by the following general formula (2):

wherein $R^7$, $R^8$, and $R^9$ are independently an unsubstituted or substituted hydrocarbon group containing 1 to 20 carbon atoms; and $R^6$ is hydrogen atom or methyl group.

2. A silyl (meth)acrylate compound containing a siloxy group according to claim 1 wherein $R^1$ and $R^2$ in the general formula (1) are independently isopropyl group or sec-butyl group.

3. A silyl (meth)acrylate compound containing a siloxy group according to claim 1 wherein $R^3$, $R^4$, and $R^5$ in the general formula (1) are independently methyl group or trimethylsiloxy group.

4. A method for producing the silyl (meth)acrylate compound containing a siloxy group of claim 1 comprising the step of reacting a chlorosilane compound containing a siloxy group having a bulky substituent represented by the following general formula (3):

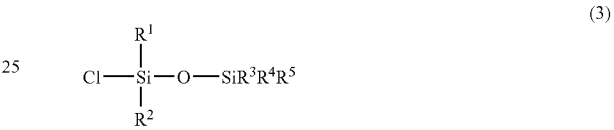
(3)

wherein $R^1$ and $R^2$ are independently a monovalent branched hydrocarbon group containing 3 to 10 carbon atoms having a hydrocarbon group at α or β position or a monovalent cyclic hydrocarbon group containing 3 to 10 carbon atoms, and $R^3$, $R^4$, and $R^5$ are independently an unsubstituted or substituted hydrocarbon group containing 1 to 20 carbon atoms or a siloxy group represented by the following general formula (2):

wherein $R^7$, $R^8$, and $R^9$ are independently an unsubstituted or substituted hydrocarbon group containing 1 to 20 carbon atoms with acrylic acid or methacrylic acid in the presence of a basic compound.

5. A method for producing a silyl (meth)acrylate compound containing a siloxy group according to claim 4 wherein a phase transfer catalyst is used.

6. A method for producing a silyl (meth)acrylate compound containing a siloxy group according to claim 4 wherein 0.5 to 2.0 mole of the chlorosilane compound of the general formula (3) is reacted per mole of the acrylic acid or methacrylic acid, and the reaction is conducted at temperature of −20° C. to 200° C.

* * * * *